United States Patent [19]
Hashimoto et al.

[11] Patent Number: 5,811,117
[45] Date of Patent: Sep. 22, 1998

[54] PERCUTANEOUSLY ABSORBABLE PREPARATION CONTAINING COHESIVE STRENGTH IMPROVING AGENT

[75] Inventors: Masaki Hashimoto, Shinnanyo; Mitsuhito Mano, Kyoto; Mutsuki Amano, Nara; Takeshi Wakiya, Soraku-gun, all of Japan

[73] Assignee: Sekisui Kagaku Kogyo Kabushiki Kaisha, Osaka, Japan

[21] Appl. No.: 750,923
[22] PCT Filed: Jul. 20, 1995
[86] PCT No.: PCT/JP95/01442
§ 371 Date: Mar. 12, 1997
§ 102(e) Date: Mar. 12, 1997
[87] PCT Pub. No.: WO96/03131
PCT Pub. Date: Feb. 8, 1996

[30] Foreign Application Priority Data
Jul. 22, 1994 [JP] Japan ................................. 6-170945

[51] Int. Cl.⁶ ............................................. A61F 13/02
[52] U.S. Cl. ............................................ 424/448; 424/449
[58] Field of Search ................................. 424/448, 449

[56] References Cited

U.S. PATENT DOCUMENTS

| | | | |
|---|---|---|---|
| 4,880,416 | 11/1989 | Horiuchi | 604/307 |
| 5,079,008 | 1/1992 | Sinnreich | 424/448 |
| 5,128,138 | 7/1992 | Blank | 424/449 |
| 5,260,064 | 11/1993 | Nakagawa | 424/448 |
| 5,650,165 | 7/1997 | Akemi | 424/448 |

FOREIGN PATENT DOCUMENTS

| | | | |
|---|---|---|---|
| 0 285 563 A1 | 10/1988 | European Pat. Off. | A61K 31/565 |
| 0 356 382 A2 | 2/1990 | European Pat. Off. | A61K 9/70 |
| 0 573 133 A1 | 12/1993 | European Pat. Off. | A61K 31/565 |
| 2-102656 | 4/1990 | Japan | A61L 15/44 |
| 3-291217 | 12/1991 | Japan | A61K 9/70 |
| 4-342532 | 11/1992 | Japan | A61K 31/57 |
| 4-360827 | 12/1992 | Japan | A61K 9/70 |
| 90/11064 | 10/1990 | WIPO | A61F 13/00 |

*Primary Examiner*—D. Gabrielle Brouillette
*Attorney, Agent, or Firm*—Pollock, Vande Sande & Priddy

[57] ABSTRACT

A percutaneously absorbable preparation which contains norethisterone, estradiol or ester thereof, each of which is highly absorbable percutaneously, can readily be stuck to the skin, and is lowly skin irritating. It is prepared by applying a pressure-sensitive adhesive layer comprising a drug and a pressure-sensitive adhesive to one side of a support. The drug comprises at least one member selected from among norethisterone, estradiol and pharmacologically acceptable esters thereof, while the adhesive comprises a copolymer composed of 20–55 mol. % of vinylpyrrolidone and 80–45 mol. % of alkyl ($C_4$–$C_{18}$) (meth)acrylate. The adhesive layer further contains a sorbifacient comprising 0.1–10 wt. % of at least one member selected from among dicarboxylic acids, hydroxy carboxylic acids, plyoxyethylene alkyl ethers and amide compounds and 5–40 wt. %, both based on the adhesive layer, of a higher fatty acid ester prepared from a $C_{10}$–$C_{18}$ fatty acid and a $C_1$–$C_{20}$ alcohol and also contains a cohesive force improver.

4 Claims, 1 Drawing Sheet

FIG. 1 ically absorbed percutaneouly, e.g.
PERCUTANEOUSLY ABSORBABLE PREPARATION CONTAINING COHESIVE STRENGTH IMPROVING AGENT This application is a 371 of PCT/JP95/01442, filed Jul. 20, 1995.

TECHNICAL FIELD

The present invention relates to a percutaneous pharmaceutical preparation with improved percutaneous absorbability and a low skin irritation.

BACKGROUND ART

Norethisterone and estradiol, inclusive of their esters, are known as female hormones. Administration of estradiol or an ester thereof is a well-established, effective treatment for the control of characteristic mental symptoms in climacteric women and prevention of osteoporosis due to loss of bone minerals. As to norethisterone or its ester, its administration is essential to the prevention of side effects of estrogens such as estradiol.

For the avoidance of adverse effects such as hepatic disorder and in view of the ease to maintain a constant blood concentration, it is preferable that such female hormones be administered percutaneously. As dosage forms suited for this purpose, U.S. Pat. No. 4,788,062 discloses a percutaneous pharmaceutical preparation utilizing a fatty acid ester such as sucrose monolaurate, glycerol monooleate, or glycerol monolaurate as an absorption enhancer. Japanese Kokai Publication Hei-4-342531 describes a percutaneous pharmaceutical preparation containing at least one member of hydroxycarboxylic acids and N-acylsarcosines as an absorption enhancer and Japanese Kokai Publication Hei-2-102656 discloses a percutaneous pharmaceutical preparation containing an amide compound and a fatty acid ester as absorption enhancers. Furthermore, directed to drug compounds which are rather easily absorbed percutaneouly, e.g. nitroglycerin, Japanese Kokai Publication Hei-3-291217 proposes a technology in which a fatty acid ester is added in a substantial proportion to an acrylic adhesive not containing a polar functional group to realize a marked improvement in absorption enhancing effect and, to further enhance the cohesive strength of the adhesive layer, a hydrophilic silicic anhydride and a hydrophobic silicic anhydride are used in combination.

However, with respect to estradiol, norethisterone, and their esters, fatty acid esters in general do not provide sufficient absorption enhancing effect, while surfactants such as hydroxycarboxylic acids and N-acylsarcosines have potent percutaneous absorption enhancing effects for these steroid hormones but have high dermal irritation proportional to their contribution to enhancing effect. Moreover, when they are used in combination with a fatty acid ester, an absorption enhancing effect commensurate with the formulated amount is obtained but the cohesive strength of the adhesive layer is decreased to cause the problem of adhesive-transfer to the skin. Moreover, in the case of an acrylic adhesive like that described in Japanese Kokai Publication Hei-3-291217, there are such problems that the low solubility of said hormones makes it impossible to add a sufficient amount of the active substance and the consequent short duration of efficacy calls for several dosings a day. Thus, the preparations provided by the conventional technologies are poor in compliance partly because, in the absence of an absorption enhancer, a large patch size is required for sufficient absorption, thus causing a feeling of physical disorder on prolonged application, and partly because the duration of efficacy is short, while the preparations with dermal permeation improved by addition of absorption enhancer satisfy the need for permeation but have the drawbacks of skin irritation and adhesive-transfer to the skin on peeling off, thus being unsuited for long-term therapy.

SUMMARY OF THE INVENTION

In view of the above state of the art, the present invention has for its object to provide a percutaneous pharmaceutical preparation which offers a high percutaneous absorbability for norethisterone, estradiol, and their esters, with satisfactory application characteristics and a low skin irritation.

The present invention relates to a percutaneous pharmaceutical preparation prepared by laminating an adhesive layer comprising an adhesive and an active ingredient to one side of a backing material, wherein said adhesive is a copolymer composed of 20 to 55 mole % of vinylpyrrolidone and 80 to 45 mole % of a $C_4$ to $C_{18}$-alkyl ester of (meth)acrylic acid, said active ingredient is at least one member selected from the group consisting of norethisterone, estradiol, and their pharmacologically acceptable esters, and said adhesive layer further comprises at least one member selected from the group consisting of dicarboxylic acids, hydroxy carboxylic acids, polyoxyethylene alkyl alcohol ethers, and amide compounds in a proportion of 0.1 to 10 weight %, based on said adhesive layer, as an absorption enhancer, a higher fatty acid ester prepared from an alcohol having 1 to 20 carbon atoms and a fatty acid having 10 to 18 carbon atoms in a proportion of 5 to 40 weight %, based on said adhesive layer, as a plasticizer, and a cohesive strength improvement agent.

1 a diffusion cell
2 a receptor tank
3 a donor tank
6 a flange
7 a sampling port
8 a skin flap
9 a magnetic stirrer
10 a percutaneous pharmaceutical preparation sample.

DETAILED DESCRIPTION OF THE INVENTION

The present invention is now described in detail.

In accordance with the present invention, the adhesive layer mentioned above comprises an active ingredient, absorption enhancers, a cohesive strength improvement agent, and an adhesive.

The active ingredient mentioned above is at least one member selected from the group consisting of norethisterone, estradiol, and their pharmacologically acceptable esters.

The concentration of said active ingredient is preferably 0.5 to 20 weight % and, for still better results, 0.5 to 15 weight %. If the concentration of the active ingredient is too high, crystals may be precipitated in the adhesive layer with time to detract from the release characteristic and stickiness to the skin of the preparation, while, if the concentration is too low, no therapeutically sufficient penetration of the active substance will be obtained without expected remedial efficacy.

The above-mentioned adhesive is a copolymer comprising vinylpyrrolidone and a $C_4$ to $C_{18}$-alkyl ester of (meth)acrylic acid as constituent components. This $C_4$ to $C_{18}$-alkyl ester of (meth)acrylic acid is not particularly restricted in kind but includes 2-ethylhexyl acrylate as a preferred example. One or more of such esters can be employed.

In said adhesive, vinylpyrrolidone accounts for 20 to 55 mole % and said $C_4$ to $C_{18}$-alkyl (meth)acrylate for 80 to 45 mole %. If the proportion of the $C_4$ to $C_{18}$-alkyl (meth)acrylate is too large and that of vinylpyrrolidone is too small, the solubility of estradiol or its ester will not be sufficiently high. On the other hand, if the proportion of said $C_4$ to $C_{18}$-alkyl (meth)acrylate is too small and that of vinylpyrrolidone is too large, the adhesive strength and, hence, stickiness to the skin will be sacrificed. The proportions are restricted to above range. The preferred proportions are 30 to 45 mole % of vinylpyrrolidone and 70 to 55 mole % of said $C_4$ to $C_{18}$-alkyl (meth)acrylate. The adhesive of the above formulation provides for satisfactory drug solubility so that a high release rate can be maintained over an extended period of time.

In accordance with the present invention, the adhesive layer further contains an absorption enhancer and a cohesive strength improvement agent.

The absorption enhancer mentioned above is at least one member selected from the group consisting of dicarboxylic acids, hydroxy carboxylic acids, polyoxyethylene alkyl alcohol ethers, and amide compounds. The dicarboxylic acids mentioned above are not particularly restricted in kind. For example, fumaric acid and maleic acid can be mentioned. Particularly preferred is fumaric acid. There is no particular restriction, either, to said hydroxy carboxylic acids. Thus, lactic acid and malic acid can be typically mentioned. Particularly preferred is lactic acid. The amide compounds are not particularly restricted in kind, either, but virtually any amide group-containing compound can be employed. Thus, for example, fatty acid ethanolamide compounds, N-acylsarcosines, etc. can be mentioned. Particularly preferred is lauric acid diethanolamide. There is no particular limitation on said polyoxyethylene alkyl alcohol ethers. For example, polyoxyethylene lauryl alcohol ether can be employed.

As to said dicarboxylic acids, hydroxy carboxylic acids, polyoxyethylene alkyl alcohol ethers, and amide compounds, one compound can be used alone or two or more compounds can be used in combination.

The concentration of said at least one member selected from the group consisting of dicarboxylic acids, hydroxy carboxylic acids, polyoxyethylene alkyl alcohol ethers, and amide compounds is 0.1 to 10 weight % based on the adhesive layer. If the concentration is less than 0.1 weight %, no sufficient absorption enhancing effect can be expected. Conversely, if the limit of 10 weight % is exceeded, the irritation of the skin will be increased although the percutaneous permeation will be increased. The preferred range is 1 to 6 weight %.

Further, another absorption enhancer is a higher fatty acid ester. When (octanol/water partition coefficient) is designated as P, log P of this higher fatty acid ester is preferably 4 to 16 in order that the distribution of the drug and absorption enhancer to the skin may be increased to thereby improve the percutaneous absorption of the active ingredient. The higher fatty acid ester is not particularly restricted in kind but is preferably a compound which is liquid at temperatures not lower than 30° C.

The higher fatty acid ester that can be used includes isopropyl myristate, isopropyl palmitate, octyldodecyl myristate, and diethyl sebacate, among others. Particularly preferred are isopropyl myristate and isopropyl palmitate.

The proportion of said higher fatty acid ester is 5 to 40 weight % based on the adhesive layer. If the proportion is smaller than 5 weight %, no sufficient absorption enhancing effect will be obtained. Conversely, if the upper limit of 40 weight % is exceeded, no sufficient cohesive strength will be obtained, thus causing the problems of adhesive-transfer to the skin and insufficient adhesive strength. The preferred range is 8 to 30 weight %.

In accordance with the present invention, the adhesive layer contains a cohesive strength improvement agent as well.

In the second aspect of the present invention, the cohesive strength improvement agent is a hydrophilic silicic anhydride. The hydrophilic silicic anhydride mentioned above preferably has a particle diameter (primary particle diameter) of not greater than 1 μm and, for still better results, not greater than 0.5 μm.

The proportion of said hydrophilic silicic anhydride is 3 to 20 weight % with respect to the adhesive layer. If the proportion is less than 3 weight %, no sufficient improvement in cohesive strength will be obtained, while a marked loss of adhesive strength will result if the upper limit of 20 weight % is exceeded. Depending on the proportions of the active ingredient, higher fatty acid ester, the composition of said adhesive, etc., the preferred range is 5 to 15 weight %.

In the third aspect of the present invention, the cohesive strength improvement agent comprises a hydrophilic silicic anhydride and a maleic anhydride group-containing copolymer.

The maleic anhydride group-containing copolymer mentioned above joins forces with said hydrophilic silicic anhydride to improve the cohesive strength lowered by the addition of said higher fatty acid ester. A hydrophobic silicic anhydride may also be added in a suitable proportion.

The proportion of said maleic anhydride group-containing copolymer may range from 0.1 to 10 weight % based on said adhesive layer, depending on the molecular weight of the copolymer, among other factors. If the proportion is smaller than 0.1 weight %, no sufficient improvement in cohesive strength will be obtained. Conversely, if the upper limit of 10 weight % is exceeded, adhesive strength will be rather decreased.

In the fourth aspect of the present invention, the cohesive strength improvement agent comprises either a polyethylene powder with a particle diameter of not greater than 50 μm or a polyethylene fiber with a monofilament length of not greater than 1 mm and a maleic anhydride group-containing copolymer.

The particle diameter of said polyethylene powder is not greater than 50 μm and the monofilament length of said polyethylene fiber is not greater than 1 mm. If the size of polyethylene particles or that of the polyethylene fiber is greater than the above-mentioned limit, no sufficient improvement in cohesive strength will be obtained.

The proportion of said polyethylene powder or polyethylene fiber is 5 to 25 weight % with respect to the adhesive layer. If the proportion is smaller than 5 weight %, no sufficient improvement in cohesive strength will be obtained. On the other hand, if the upper limit of 25 weight % is exceeded, no sufficient adhesive strength will be realized. Depending on the proportion of said fatty acid ester etc., the preferred range is 8 to 20 weight %.

In the fifth aspect of the present invention, the cohesive strength improvement agent comprises a hydrophilic silicic anhydride and a polyhydric alcohol.

The polyhydric alcohol mentioned above is not particularly restricted in kind. Thus, for example, polyvinyl alcohol, polyethylene glycol, glycerin, etc. can be employed. Preferably, any one or more of polyvinyl alcohol, polyethylene glycol, and glycerin are employed.

The proportion of said polyhydric alcohol is 1 to 40 weight % with respect to the adhesive layer. If the proportion is less than 1 weight %, no sufficient improvement in cohesive strength will be obtained. If the upper limit of 40 weight % is exceeded, adhesive strength will be decreased. Depending on the formulation of said adhesive, and the relative amounts of said active ingredient, higher fatty acid ester, and hydrophilic silicic anhydride, etc., the proportion of the polyhydric alcohol is preferably 1 to 30 weight % and, for still better results, 3 to 10 weight %.

In the sixth aspect of the present invention, the cohesive strength improvement agent comprises a hydrophilic silicic anhydride and a polycarboxylic acid.

The polycarboxylic acid mentioned above is not restricted in kind. Thus, for example, fumaric acid, citric acid, and polyacrylic acid can be mentioned. It is preferable to use either polyacrylic acid or citric acid or both.

The proportion of said polycarboxylic acid is 0.5 to 20 weight % based on the adhesive layer. If the proportion is smaller than 0.5 weight %, no sufficient improvement in cohesive strength will be obtained. On the other hand, if the proportion exceeds 20 weight %, adhesive strength will be decreased. Depending on the formulation of said adhesive, the relative amounts of said active ingredient, fatty acid ester, and hydrophilic silicic anhydride, among other factors, the preferred range is 1 to 10 weight %.

The backing material that can be used in accordance with the present invention is not critical in kind only if it is flexible and impermeable to the active ingredient. Thus, for example, a film of polyethylene, polyurethane, polyethylene terephthalate, vinyl acetate-ethylene copolymer, or the like, which may optionally have been treated to preclude diffusion of the active ingredient. The thickness of the backing material is generally not greater than 500 $\mu$m and is preferably 2 to 150 $\mu$m.

The percutaneous pharmaceutical preparation of the present invention can be manufactured by the conventional processes for the production of adhesive tapes. Thus, for example, any of the solvent, hot-melt, and electron beam-curing emulsion processes can be employed. Particularly preferred is the solvent process.

The adhesive layer is constructed generally in a thickness of 20 to 200 $\mu$m, although the optional thickness varies with different applications.

The release lines for the percutaneous pharmaceutical preparation are not particularly restricted in kind but can for example be a silicon-treated polyethylene terephthalate film.

While the amount of dermal permeation of the active ingredient depends on the diffusion in the adhesive layer as well as the distribution (partition) to the skin of the active ingredient, the higher fatty acid ester accounting for a large proportion of the adhesive layer of the invention not only improves the diffusion of the active ingredient in the adhesive layer but also improves the distribution of the active ingredient and of the absorption enhancer which is incorporated in a small proportion to thereby enhance the dermal permeation of the active ingredient. In addition, the higher fatty acid ester helps to reduce the amount of the absorption enhancer necessary to obtain the required permeation of the drug substance and thereby decrease the skin irritation.

Although the use of said higher fatty acid in a large proportion otherwise causes a marked decrease in cohesive strength of the adhesive layer and the consequent problem of adhesive-transfer to the skin, the decrease in cohesive strength and the problem of adhesive-transfer to the skin can be obviated by the use of a hydrophilic silicic anhydride, use of a hydrophilic silicic anhydride in combination with a maleic anhydride group-containing copolymer, use of a maleic anhydride group-containing copolymer in combination with a polyethylene powder or fiber, or use of a hydrophilic silicic anhydride in combination with a polyalcohol or a polycarboxylic acid.

BEST MODE FOR CARRYING OUT THE INVENTION

The following examples and comparative examples are intended to describe the present invention in further detail and should by no means be construed as defining the scope of the invention.

EXAMPLE 1

A separable flask was charged with 65 mole % (302.0 g) of 2-ethylhexyl acrylate (hereinafter sometimes referred to briefly as EHA), 35 mole % of vinylpyrrolidone (hereinafter sometimes referred to briefly as VP), and 0.02 weight % (40.0 mg) of hexamethylene glycol dimethacrylate, followed by addition of 70.6 g of ethyl acetate so that the monomer concentration at the start of polymerization was 85 weight %. This solution was heated to 60° C. under nitrogen gas, the polymerization initiator lauroyl peroxide and ethyl acetate were added sequentially in small portions, and the polymerization reaction was carried out for 32 hours. The polymer slurry was withdrawn, and then, an alcoholic dispersion of norethisterone acetate, isopropyl myristate, lauric acid diethanolamide, and hydrophilic silicic anhydride was added to make nonvolatile matter concentration of 20 weight % (the sum of the weight of the polymer after removal of ethyl acetate and alcohol and the weight of norethisterone acetate etc.) and in such proportions that the concentrations of norethisterone acetate, isopropyl myristate, lauric acid diethanolamide, and hydrophilic silicic anhydride in the nonvolatile matter are 3 weight %, 25 weight %, 3 weight %, and 10 weight %, respectively, and the mixture was stirred.

This solution was coated on a 35 $\mu$m-thick silicon-treated polyethylene terephthalate (hereinafter referred to briefly as PET) film in a dry thickness of about 60 $\mu$m and dried. To this dry coated film was laminated on an approximately 35 $\mu$m-thick polyethylene terephthalate-ethylene vinyl acetate (hereinafter referred to briefly as PET-EVA) laminate film to provide a percutaneous pharmaceutical preparation.

This percutaneous pharmaceutical preparation was evaluated for the following parameters. The results are presented in Table 1.

Dermal Permeation

Figure 1:
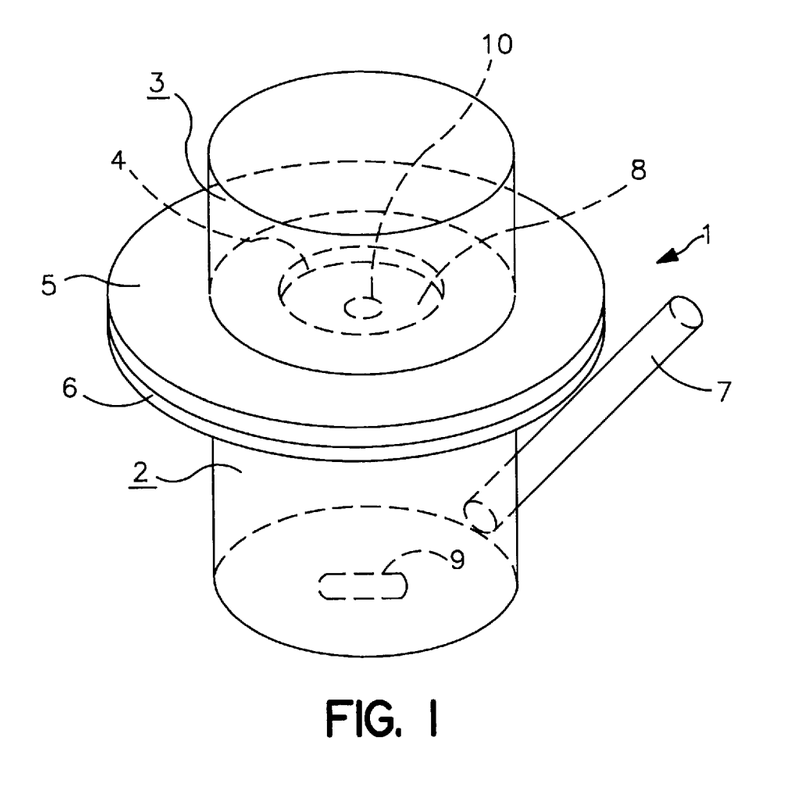
FIG. 1 is a perspective view showing a percutaneous drug permeation test cell.

After a hairless mouse (6 weeks old, male) was sacrificed by cervical dislocation, the skin specimen was isolated and subcutaneous adipose tissue was removed. The skin specimen was immediately set in a percutaneous drug permeation test cell. The apparatus used for this test is illustrated in FIG. 1. A test sample punched out (20 mm in diameter) was attached to the top of the apparatus and the receptor tank below was filled with a buffer solution. The apparatus was then installed in an incubator controlled at 37° C. from the start of the experiment. At 3, 20, and 24 hours after the beginning of the experiment, 1 ml portions of the solution in the receptor tank were sampled and immediately after each sampling the tank was supplemented with 1 ml of the fresh buffered solution. Using these samples, the amount of the active ingredient that had permeated through the hairless mouse skin into the receptor tank was determined to evaluate the dermal permeation. Three samples were used for each test.

Cohesive Strength

In accordance with JIS Z 0237-1980, the holding power of each preparation was measured to evaluate the cohesive strength. However, because a slip load of 1000 g was unrealistically high for a percutaneous pharmaceutical preparation, the load of 500 g was used in this test.

EXAMPLE 2

Except that 5 weight % of 17-β-estradiol was used in addition to norethisterone acetate and lactic acid was used in lieu of lauric acid diethanolamide, the procedure of Example 1 was otherwise repeated to provide a percutaneous pharmaceutical preparation.

This percutaneous pharmaceutical preparation was evaluated as in Example 1 and, in addition, the following evaluations were made. The results were shown in Table 1.

Dermal Irritation

The back of rabbits (Japanese white strain) was clipped with an electric clipper and shaved with an electric shaver. A 12 cm$^2$ punched-out sample (30 mm×41 mm) of the percutaneous pharmaceutical preparation was attached to the rabbit back and kept for 48 hours. Thereafter, the percutaneous pharmaceutical preparation was peeled off and the intensity of erythema was evaluated at 1 and 24 hours after peeling off. Six samples were used for each test and the mean value was shown.
(Evaluation criteria for erythema)

0: No erythema
1: Barely discernible, slight erythema
2: Definite erythema
3: Moderate erythema
4: Scarlet, intense erythema

EXAMPLE 3

Except for using fumaric acid in lieu of lauric acid diethanolamide, the procedure of Example 1 was otherwise repeated to provide a percutaneous pharmaceutical preparation. This absorbable preparation was evaluated for the parameters indicated in Table 1. The results are also shown in Table 1.

EXAMPLE 4

Except that 2 weight % of methoxyethylene-maleic anhydride copolymer was added, the proportion of hydrophilic silicic anhydride was altered to 5 weight %, and isopropyl palpitate was used in lieu of isopropyl myristate, the procedure of Example 2 was otherwise repeated to provide a percutaneous pharmaceutical preparation and evaluate it. The results are presented in Table 1.

EXAMPLE 5

Except that diethyl sebacate was used in lieu of isopropyl myristate, the procedure of Example 1 was otherwise repeated to provide a percutaneous pharmaceutical preparation.

This absorbable preparation was evaluated for the parameters indicated in Table 1. The results are also presented in Table 1.

EXAMPLE 6

Except that octyldodecyl myristate was used in lieu of isopropyl myristate, the procedure of Example 1 was otherwise repeated to provide a percutaneous pharmaceutical preparation and evaluate it. The results are presented in Table 1.

EXAMPLE 7

Except that isopropyl myristate was used in a proportion of 10 weight %, the procedure of Example 1 was otherwise repeated to provide a percutaneous pharmaceutical preparation and evaluate it. The results are presented in Table 1.

EXAMPLE 8

Except that isopropyl palmitate was used in a proportion of 35 weight %, the procedure of Example 4 was otherwise repeated to provide a percutaneous pharmaceutical preparation and evaluate it. The results are presented in Table 1.

EXAMPLE 9

Except that 1 weight % of lauric acid diethanolamide was used in lieu of lactic acid, the procedure of Example 2 was otherwise repeated to provide a percutaneous pharmaceutical preparation. This absorbable preparation was evaluated for the parameters indicated in Table 1. The results are presented in Table 1.

EXAMPLE 10

A separable flask was charged with 60 mole % (234.8 g) of EHA, 40 mole % (115.3 g) of VP, and 0.02 weight % (70.0 mg) of hexamethylene glycol dimethacrylate, followed by addition of 61.8 g of ethyl acetate so that the monomer concentration at the start of polymerization was 85 weight %. This solution was heated at 60° C. under nitrogen gas and the polymerization initiator lauroyl peroxide and ethyl acetate were added sequentially in small portions. The polymerization reaction was conducted for 32 hours. The polymer slurry was withdrawn, and to this polymer slurry was added an alcoholic dispersion of norethisterone acetate, isopropyl myristate, lauric acid diethanolamide, methoxyethylene-maleic anhydride copolymer, and hydrophilic silicic anhydride at a final concentration of a non-volatile matter of 20 weight % (the sum of the weight of the polymer after removal of ethyl acetate and alcohol and the weight of norethisterone acetate etc.) and in such proportions that the concentrations of norethisterone acetate, isopropyl myristate, lauric acid diethanolamide, methoxyethylene-maleic anhydride copolymer, and hydrophilic silicic anhydride in the nonvolatile matter were 7 weight %, 20 weight %, 1.5 weight %, 1 weight %, and 3 weight %, respectively, and the mixture was stirred.

This solution was coated on a 35 μm-thick silicon-treated PET film in a dry thickness of about 60 μm and dried.

To this dry coated film was laminated an approximately 35 μm-thick PET-EVA laminate film to provide a percutaneous pharmaceutical preparation.

This percutaneous pharmaceutical preparation obtained was evaluated as in Example 1. The results are presented in Table 1.

In Tables 1 to 5, MEMA stands for methoxyethylene-maleic anhydride copolymer, NA for norethisterone acetate, E2 for estradiol, LD for lauric acid diethanolamide, POE for polyoxyethylene lauryl alcohol ether, IPM for isopropyl myristate, IPP for isopropyl palmitate, DES for diethyl sebacate, and ODM for octyldodecyl myristate.

TABLE 1

| | EHA/VP | Absorption enhancer | | Fatty acid ester | | Silicic anhydride | MEMA | NA | E2 | Dermal permeation $\mu g/cm^2$ | | Skin irri- | Hold- ing power |
|---|---|---|---|---|---|---|---|---|---|---|---|---|---|
| | Molar ratio | Species | Wt. % | Species | Wt. % | Wt. % | Wt. % | Wt. % | Wt. % | NA | E2 | tation | (min.) |
| Example | | | | | | | | | | | | | |
| 1 | 65/35 | LD | 3 | IPM | 25 | 10 | — | 3 | — | 26 | — | — | 28 |
| 2 | 65/35 | Lactic acid | 3 | IPM | 25 | 10 | — | 3 | 5 | 27 | 8 | 1.2 | 31 |
| 3 | 65/35 | Fumaric acid | 3 | IPM | 25 | 10 | — | 3 | — | 21 | — | 1.2 | 33 |
| 4 | 65/35 | Lactic acid | 3 | IPP | 25 | 5 | 2 | 3 | 5 | 26 | 8 | 1.1 | 28 |
| 5 | 65/35 | LD | 3 | DES | 25 | 10 | — | 3 | — | 23 | — | 1.1 | 26 |
| 6 | 65/35 | LD | 3 | ODM | 25 | 10 | — | 3 | — | 23 | — | — | 23 |
| 7 | 65/35 | LD | 3 | IPM | 10 | 10 | — | 3 | — | 21 | — | — | 32 |
| 8 | 65/35 | Lactic acid | 3 | IPP | 35 | 5 | 2 | 3 | 5 | 25 | 8 | — | 21 |
| 9 | 65/35 | LD | 1 | IPM | 25 | 10 | — | 3 | 5 | 24 | 7 | — | 31 |
| 10 | 60/40 | LD | 1.5 | IPM | 20 | 3 | 1 | 7 | — | 23 | — | — | 32 |

EXAMPLE 11

A separable flask was charged with 80 mole % (371.7 g) of EHA, 20 mole % (56.0 g) of VP, and 0.02 weight % (85.5 mg) of hexamethylene glycol dimethacrylate, followed by addition of 75.5 g of ethyl acetate, so that the monomer concentration at the start of polymerization was 85 weight %. This solution was heated at 60° C. under nitrogen gas and the polymerization initiator lauroyl peroxide and ethyl acetate were added sequentially in small portions. The polymerization reaction was conducted for 32 hours. The polymer slurry was withdrawn, and to this polymer slurry was added an alcoholic dispersion of norethisterone acetate, isopropyl myristate, lauric acid diethanolamide, and hydrophilic silicic anhydride at a final concentration of a nonvolatile matter of 20 weight % (the sum of the weight of the polymer after removal of ethyl acetate and alcohol and the weight of norethisterone acetate etc.) and in such proportions that the concentrations of norethisterone acetate, isopropyl myristate, lactic acid, and hydrophilic silicic anhydride in the nonvolatile matter were 5 weight %, 20 weight %, 2 weight %, and 15 weight %, respectively, and the mixture was stirred.

This solution was coated on a 35 μm-thick silicon-treated PET film in a dry thickness of about 60 μm and dried.

To this dry coated film was laminated an approximately 35 μm-thick PET-EVA laminate film to provide a percutaneous pharmaceutical preparation.

This percutaneous pharmaceutical preparation obtained was evaluated as in Example 1. The results are presented in Table 2.

EXAMPLE 12

Except for using 2 weight % of polyoxyethylene(9) lauryl alcohol ether in lieu of lactic acid, the procedure of Example 2 was repeated to provide a percutaneous pharmaceutical preparation and evaluate it. The results are presented in Table 2.

COMPARATIVE EXAMPLE 1

Except that neither lauric acid diethanolamide nor isopropyl myristate was used, the procedure of Example 1 was repeated to provide a percutaneous pharmaceutical preparation and evaluate it for the parameters indicated in Table 2. The results are presented in Table 2.

COMPARATIVE EXAMPLE 2

Except that isopropyl myristate was used in a proportion of 3 weight %, the procedure of Example 2 was repeated to provide a percutaneous pharmaceutical preparation and evaluate it. The results are presented in Table 2.

COMPARATIVE EXAMPLE 3

Except that hydrophilic silicic anhydride was not used, the procedure of Example 1 was repeated to provide a percutaneous pharmaceutical preparation and evaluate it for the parameters indicated in Table 2. The results are presented in Table 2.

COMPARATIVE EXAMPLE 4

Except that hydrophilic silicic anhydride was used in a proportion of 0.5 weight %, the procedure of Example 1 was otherwise repeated to provide a percutaneous pharmaceutical preparation and evaluate it. The results are presented in Table 2.

COMPARATIVE EXAMPLE 5

Except that lauric acid diethanolamide was used in a proportion of 6 weight % and 17-β-estradiol was added in a proportion of 5 weight %, the procedure of Example 1 was otherwise repeated to provide a percutaneous pharmaceutical preparation and evaluate it for the parameters indicated in Table 2. The results are also presented in Table 2.

COMPARATIVE EXAMPLE 6

Except that isopropyl myristate was not used, the procedure of Example 13 was otherwise repeated to provide a percutaneous pharmaceutical preparation and evaluate it for the parameters indicated in Table 2. The results are also presented in Table 2.

COMPARATIVE EXAMPLE 7

Except that lauric acid diethanolamide was not added, the procedure of Example 1 was otherwise repeated to provide a percutaneous pharmaceutical preparation and evaluate it for the parameters indicated in Table 2. The results are also presented in Table 2.

TABLE 2

| | EHA/VP Molar ratio | Absorption enhancer Species | Wt. % | Fatty acid ester Species | Wt. % | Silicic anhydride Wt. % | NA Wt. % | E2 Wt. % | Dermal permeation $\mu g/cm^2$ NA | Dermal permeation $\mu g/cm^2$ E2 | Skin irritation | Holding power (min.) |
|---|---|---|---|---|---|---|---|---|---|---|---|---|
| Example | | | | | | | | | | | | |
| 11 | 80/20 | Lactic acid | 2 | IPM | 20 | 15 | 5 | — | 22 | — | — | 30 |
| 12 | 65/35 | POE | 2 | IPM | 25 | 10 | 3 | 5 | 25 | 6 | 1.0 | 24 |
| Comparative Example | | | | | | | | | | | | |
| 1 | 65/35 | — | — | — | — | 10 | 3 | — | 6 | — | 0.9 | 38 |
| 2 | 65/35 | Lactic acid | 3 | IPM | 3 | 10 | 3 | 5 | 12 | 3 | 1.1 | 27 |
| 3 | 65/35 | LD | 3 | IPM | 25 | — | 3 | — | 20 | — | 1.3 | 5 |
| 4 | 65/35 | LD | 3 | IPM | 25 | 0.5 | 3 | — | 18 | — | — | 8 |
| 5 | 65/35 | LD | 6 | IPM | 25 | 10 | 3 | 5 | 18 | 10 | 3.0 | 38 |
| 6 | 65/35 | POE | 2 | — | — | 10 | 3 | 5 | 8 | 8 | — | 35 |
| 7 | 65/35 | — | — | IPM | 25 | 10 | 3 | — | 13 | — | — | 31 |

EXAMPLE 13

A separable flask was charged with 65 mole % (302.2 g) of EHA, 35 mole % (98.0 g) of VP, and 0.02 weight % (40.0 mg) of hexamethylene glycol dimethacrylate, followed by addition of 70.6 g of ethyl acetate, so that the monomer concentration at the start of polymerization was 85 weight %. The solution was heated at 60° C. under nitrogen gas and the polymerization initiator lauroyl peroxide and ethyl acetate were added sequentially in small portions. The polymerization reaction was conducted for 32 hours. The polymer slurry was withdrawn, and to this polymer slurry was added a tetrahydrofuran dispersion of norethisterone acetate, isopropyl myristate, lauric acid diethanolamide, and polyethylene powder at a final concentration of a nonvolatile matter of 20 weight % (the sum of the weight of the polymer after removal of ethyl acetate and tetrahydrofuran and the weight of norethisterone acetate etc.) and in such proportions that the concentrations of norethisterone acetate, isopropyl myristate, lauric acid diethanolamide, and polyethylene powder in the nonvolatile matter were 3 weight %, 20 weight %, 3 weight %, and 15 weight %, respectively, and the mixture was stirred.

This solution was coated on a 35 $\mu$m silicon-treated PET film in a dry thickness of about 60 $\mu$m and dried. To this coated film was laminated an approximately 35 $\mu$m-thick PET-EVA laminate film to provide a percutaneous pharmaceutical preparation.

The percutaneous pharmaceutical preparation obtained was evaluated as in Example 1. The results are presented in Table 3.

EXAMPLE 14

Except that 5 weight % of 17-β-estradiol was added and lactic acid was used in lieu of lauric acid diethanolamide, the procedure of Example 14 was otherwise repeated to provide a percutaneous pharmaceutical preparation and evaluate it for the parameters indicated in Table 3. The results are also presented in Table 3.

EXAMPLE 15

Except that fumaric acid was used in lieu of lauric acid diethanolamide, the procedure of Example 14 was otherwise repeated to provide a percutaneous pharmaceutical preparation and evaluate it for the parameters indicated in Table 3. The results are also presented in Table 3.

EXAMPLE 16

Except that isopropyl palmitate was used in lieu of isopropyl myristate, the procedure of Example 15 was repeated to provide a percutaneous pharmaceutical preparation and evaluate it. The results are presented in Table 3.

EXAMPLE 17

Except that 10 weight % of a polyethylene fiber with a monofilament length of about 0.5 mm was used in lieu of the polyethylene powder, the procedure of Example 16 was repeated to provide a percutaneous pharmaceutical preparation and evaluate it. The results are presented in Table 3.

COMPARATIVE EXAMPLE 8

Except that neither lauric acid diethanolamide nor isopropyl myristate was used, the procedure of Example 14 was otherwise repeated to provide a percutaneous pharmaceutical preparation and evaluate it for the parameters indicated in Table 3. The results are also presented in Table 3.

COMPARATIVE EXAMPLE 9

Except that the proportion of isopropyl myristate was altered to 3 weight %, the procedure of Example 15 was otherwise repeated to provide a percutaneous pharmaceutical preparation and evaluate it. The results are presented in Table 3.

COMPARATIVE EXAMPLE 10

Except that the polyethylene powder was not used, the procedure of Example 14 was otherwise repeated to provide a percutaneous pharmaceutical preparation and evaluate it for the parameters indicated in Table 3. The results are also presented in Table 3.

COMPARATIVE EXAMPLE 11

Except that the methoxyethylene-maleic anhydride copolymer was not used, the procedure of Example 14 was otherwise repeated to provide a percutaneous pharmaceutical preparation and evaluate it for the parameters indicated in Table 3. The results are also presented in Table 3.

COMPARATIVE EXAMPLE 12

Except that 6 weight % of lauric acid diethanolamide was used in lieu of lactic acid, the procedure of Example 15 was otherwise repeated to provide a percutaneous pharmaceutical preparation and evaluate it for the parameters indicated in Table 3. The results are also presented in Table 3.

of Example 19 was otherwise repeated to provide a percutaneous pharmaceutical preparation and evaluate it. The results are presented in Table 4.

TABLE 3

|  | Absorption enhancer | | Fatty acid ester | | Polyethylene | NA | E2 | Dermal permeation $\mu g/cm^2$ | | Skin irri- | Hold- ing power |
| --- | --- | --- | --- | --- | --- | --- | --- | --- | --- | --- | --- |
|  | Species | Wt. % | Species | Wt. % | Wt. % | Wt. % | Wt. % | NA | E2 | tation | (min.) |
| Example |  |  |  |  |  |  |  |  |  |  |  |
| 13 | LD | 3 | IPM | 20 | 15 | 3 | — | 23 | — | — | 21 |
| 14 | Lactic acid | 3 | IPM | 20 | 15 | 3 | 8 | 24 | 9 | 1.2 | 23 |
| 15 | Fumaric acid | 3 | IPM | 20 | 15 | 3 | — | 21 | — | 1.2 | 25 |
| 16 | Lactic acid | 3 | IPP | 20 | 15 | 3 | 8 | 25 | 8 | 1.1 | 22 |
| 17 | Fumaric acid | 3 | IPM | 20 | 10 | 3 | — | 23 | — | 1.1 | 19 |
| Comparative Example |  |  |  |  |  |  |  |  |  |  |  |
| 8 | — | — | — | — | 15 | 3 | — | 5 | — | 1.2 | 35 |
| 9 | Lactic acid | 3 | IPM | 3 | 15 | 3 | 8 | 10 | 3 | 1.1 | 32 |
| 10 | LD | 3 | IPM | 20 | — | 3 | — | 21 | — | 1.2 | 4 |
| 11 | LD | 3 | IPM | 20 | 15 | 3 | — | 20 | — | 1.3 | 2 |
| 12 | LD | 6 | IPM | 20 | 15 | 3 | 8 | 18 | 9 | 3.0 | 37 |

EXAMPLE 18

A separable flask was charged with 65 mole % (302.0 g) of EHA, 35 mole % (98.0 g) of VP, and 0.02 weight % (40.0 mg) of hexamethylene glycol dimethacrylate, followed by addition of 70.6 g of ethyl acetate so that the monomer concentration at the start of polymerization was 85 weight %. This solution was heated at 60° C. under nitrogen gas and the polymerization initiator lauroyl peroxide and ethyl acetate were added sequentially in small portions. The polymerization reaction was conducted for 32 hours. The polymer slurry was withdrawn, and to this polymer slurry was added an alcoholic dispersion of norethisterone acetate, isopropyl myristate, lauric acid diethanolamide, polyvinyl alcohol, and hydrophilic silicic anhydride at a final concentration of a nonvolatile matter of 20 weight % (the sum of the weight of the polymer after removal of ethyl acetate and alcohol and the weight of norethisterone acetate etc.) and in such proportions that the concentrations of norethisterone acetate, isopropyl myristate, lauric acid diethanolamide, polyvinyl alcohol, and hydrophilic silicic anhydride in the nonvolatile matter were 3 weight %, 25 weight %, 3 weight %, 5 weight %, and 5 weight %, respectively, and the mixture was stirred.

This solution was coated on a 35 μm-thick silicon-treated PET film in a dry thickness of about 60 μm and dried.

To this coated film was laminated an approximately 35 μm-thick PET-EVA laminate film to provide a percutaneous pharmaceutical preparation.

This percutaneous pharmaceutical preparation was evaluated as in Example 2. The results are presented in Table 4.

EXAMPLE 19

Except that polyethylene glycol (mol. wt. 400) was used in lieu of polyvinyl alcohol, the procedure of Example 19 was otherwise repeated to provide a percutaneous pharmaceutical preparation and evaluate it. The results are presented in Table 4.

EXAMPLE 20

Except that 5 weight % of 17-β-estradiol was added and glycerin was used in lieu of polyvinyl alcohol, the procedure of Example 19 was otherwise repeated to provide a percutaneous pharmaceutical preparation and evaluate it. The results are presented in Table 4.

EXAMPLE 21

Except that the proportion of polyvinyl alcohol was altered to 3 weight %, the procedure of Example 19 was otherwise repeated to provide a percutaneous pharmaceutical preparation and evaluate it. The results are presented in Table 4.

EXAMPLE 22

Except that the proportion of polyvinyl alcohol was altered to 10 weight %, the procedure of Example 19 was otherwise repeated to provide a percutaneous pharmaceutical preparation and evaluate it. The results are presented in Table 4.

COMPARATIVE EXAMPLE 13

Except that neither lauric acid diethanolamide nor isopropyl myristate was used and 5 weight % of 17- β-estradiol was added, the procedure of Example 19 was otherwise repeated to provide a percutaneous pharmaceutical preparation and evaluate it. The results are presented in Table 4.

COMPARATIVE EXAMPLE 14

Except that hydrophilic silicic anhydride was not used, the procedure of Example 19 was otherwise repeated to provide a percutaneous pharmaceutical preparation and evaluate it. The results are presented in Table 4.

COMPARATIVE EXAMPLE 15

Except that polyvinyl alcohol was not used, the procedure of Example 19 was otherwise repeated to provide a percutaneous pharmaceutical preparation and evaluate it. The results are presented in Table 4.

COMPARATIVE EXAMPLE 16

Except that the proportion of lauric acid diethanolamide was altered to 6 weight %, 17-β-estradiol was added in a proportion of 8 weight %, and isopropyl myristate was not used, the procedure of Example 19 was otherwise repeated to provide a percutaneous pharmaceutical preparation and evaluate it. The results are presented in Table 4.

In Table 4, PVA stands for polyvinyl alcohol (tradename: Poval), PEG for polyethylene glycol, and GLY for glycerin.

EXAMPLE 25

Except that 17-β-estradiol was added in a proportion of 5 weight %, the procedure of Example 24 was otherwise repeated to provide a percutaneous pharmaceutical preparation and evaluate it. The results are presented in Table 5.

TABLE 3

| | Absorption enhancer | | Fatty acid ester | | Silicic anhydride | Polycarbonic acid | | NA | E2 | Dermal permeation $\mu g/cm^2$ | | Skin irri- | Hold- ing power |
|---|---|---|---|---|---|---|---|---|---|---|---|---|---|
| | Species | Wt. % | Species | Wt. % | Wt. % | Species | Wt. % | Wt. % | Wt. % | NA | E2 | tation | (min.) |
| Example | | | | | | | | | | | | | |
| 18 | LD | 3 | IPM | 25 | 5 | PVA | 5 | 3 | — | 25 | — | 1.2 | 20 |
| 19 | LD | 3 | IPM | 25 | 5 | PEG | 5 | 3 | — | 22 | — | 1.1 | 17 |
| 20 | LD | 3 | IPM | 25 | 5 | GLY | 5 | 3 | 5 | 24 | 9 | 1.0 | 19 |
| 21 | LD | 3 | IPM | 25 | 5 | PVA | 3 | 3 | — | 23 | — | 0.9 | 14 |
| 22 | LD | 3 | IPM | 25 | 5 | PVA | 10 | 3 | — | 22 | — | 1.2 | 38 |
| Compara- tive Example | | | | | | | | | | | | | |
| 13 | — | — | — | — | 5 | PVA | 5 | 3 | 5 | 5 | 3 | 1.0 | 35 |
| 14 | LD | 3 | IPM | 25 | — | PVA | 5 | 3 | — | 20 | — | 1.3 | <1 |
| 15 | LD | 3 | IPM | 25 | 5 | — | — | 3 | — | 21 | — | 1.4 | <1 |
| 16 | LD | 6 | — | — | 5 | PVA | 5 | 5 | 5 | 23 | 8 | 3.0 | 38 |

A separable flask was charged with 65 mole % (302.0 g) of EHA, 35 mole % (98.0 g) of VP, and 0.02 weight % (40.0 mg) of hexamethylene glycol dimethacrylate, followed by addition of 70.6 g of ethyl acetate so that the monomer concentration at the start of polymerization was 85 weight %. This solution was heated at 60° C. under nitrogen gas and the polymerization initiator lauroyl peroxide and ethyl acetate were added sequentially in small portions. The polymerization reaction was conducted for 32 hours. The polymer slurry was withdrawn, and to this polymer slurry was added an alcoholic dispersion of norethisterone acetate, isopropyl myristate, lauric acid diethanolamide, polyacrylic acid, and hydrophilic silicic anhydride at a final concentration of a nonvolatile matter of 20 weight % (the sum of the weight of the polymer after removal of ethyl acetate and alcohol and the weight of norethisterone acetate etc.) and in such proportions that the concentrations of norethisterone acetate, isopropyl myristate, lauric acid diethanolamide, polyacrylic acid, and hydrophilic silicic anhydride in the nonvolatile matter were 3 weight %, 30 weight %, 3 weight %, 3 weight %, and 10 weight %, respectively, and the mixture was stirred.

This solution was coated on a 35 μm-thick silicon-treated PET film in a dry thickness of about 60 μm and dried.

To this dry coated film was laminated an approximately 35 μm-thick PET-EVA laminate film to provide a percutaneous pharmaceutical preparation.

This percutaneous pharmaceutical preparation was evaluated as in Example 2. The results are presented in Table 5.

EXAMPLE 24

Except that citric acid was used in lieu of polyacrylic acid, the procedure of Example 24 was otherwise repeated to provide a percutaneous pharmaceutical preparation and evaluate it. The results are presented in Table 5.

EXAMPLE 26

Except that the proportion of polyacrylic acid was altered to 1 weight %, the procedure of Example 24 was otherwise repeated to provide a percutaneous pharmaceutical preparation and evaluate it. The results are presented in Table 5.

EXAMPLE 27

Except that the proportion of hydrophilic silicic anhydride was altered to 5 weight %, the procedure of Example 24 was otherwise repeated to provide a percutaneous pharmaceutical preparation and evaluate it. The results are presented in Table 5.

COMPARATIVE EXAMPLE 17

Except that neither lauric acid diethanolamide nor isopropyl myristate was used, the procedure of Example 24 was otherwise repeated to provide a percutaneous pharmaceutical preparation and evaluate it. The results are presented in Table 5.

COMPARATIVE EXAMPLE 18

Except that hydrophilic silicic anhydride was not used, the procedure of Example 24 was otherwise repeated to provide a percutaneous pharmaceutical preparation and evaluate it. The results are presented in Table 5.

COMPARATIVE EXAMPLE 19

Except that polyacrylic acid was not used, the procedure of Example 24 was otherwise repeated to provide a percutaneous pharmaceutical preparation and evaluate it. The results are presented in Table 5.

COMPARATIVE EXAMPLE 20

Except that the proportion of lauric acid diethanolamide was altered to 6 weight % and 17-β-estradiol was added in a proportion of 5 weight %, the procedure of Example 24 was otherwise repeated to provide a percutaneous pharmaceutical preparation and evaluate it. The results are presented in Table 5.

In Table 5, PAA stands for polyacrylic acid.

TABLE 5

| | Absorption enhancer | | Fatty acid ester | | Silicic anhydride | Polycarbonic acid | | NA | E2 | Dermal permeation $\mu g/cm^2$ | | Skin irri- tation | Hold- ing power (min.) |
|---|---|---|---|---|---|---|---|---|---|---|---|---|---|
| | Species | Wt. % | Species | Wt. % | Wt. % | Species | Wt. % | Wt. % | Wt. % | NA | E2 | | |
| Example | | | | | | | | | | | | | |
| 23 | LD | 3 | IPM | 30 | 10 | PAA | 3 | 3 | — | 26 | — | 1.1 | 40 |
| 24 | LD | 3 | IPM | 30 | 10 | citric acid | 3 | 3 | — | 24 | — | 1.2 | 30 |
| 25 | LD | 3 | IPM | 30 | 10 | PAA | 3 | 3 | 5 | 25 | 9 | 1.0 | 34 |
| 26 | LD | 3 | IPM | 30 | 10 | PAA | 1 | 3 | — | 24 | — | 0.9 | 35 |
| 27 | LD | 3 | IPM | 30 | 5 | PAA | 3 | 3 | — | 23 | — | 1.0 | 25 |
| Comparative Example | | | | | | | | | | | | | |
| 17 | — | — | — | — | 10 | PAA | 3 | 3 | — | 4 | — | 1.1 | 51 |
| 18 | LD | 3 | IPM | 30 | — | PAA | 3 | 3 | — | 22 | — | 1.2 | 10 |
| 19 | LD | 3 | IPM | 30 | 10 | — | — | 3 | — | 23 | — | 0.9 | 1 |
| 20 | LD | 6 | IPM | 30 | 10 | PAA | 3 | 3 | 5 | 24 | 8 | 3.1 | 40 |

The results obtained in the above examples indicate that the preparation of the present invention insures a high dermal permeation of norethisterone and estradiol with low skin irritation and satisfactory adhesive strength.

INDUSTRIAL APPLICABILITY

Constituted as described above, the present invention provides a percutaneous pharmaceutical preparation which insures a high transdermal absorbability of norethisterone, estradiol and their esters, with satisfactory adhesive strength with improved cohesive strength, and low dermal irritation.

We claim:

1. A percutaneous pharmaceutical preparation prepared by laminating an adhesive layer comprising an adhesive and an active ingredient to one side of a backing material,
   wherein said adhesive is a copolymer composed of 20 to 55 mole % of vinylpyrrolidone and 80 to 45 mole % of a $C_4$ to $C_{18}$-alkyl ester of (meth)acrylic acid,
   said active ingredient is at least one member selected from the group consisting of norethisterone, estradiol, and their pharmacologically acceptable esters, and
   said adhesive layer further comprises:
      at least one member selected from the group consisting of dicarboxylic acids, hydroxy carboxylic acids, polyoxyethylene alkyl alcohol ethers, fatty acid ethanolamide compounds and N-acylsarcosines in a proportion of 0.1 to 10 weight %, based on the adhesive layer, as an absorption enhancer,
      a higher fatty acid ester prepared from a fatty acid having 10 to 18 carbon atoms and an alcohol having 1 to 20 carbon atoms in a proportion of 5 to 40 weight %, based on said adhesive layer, as another absorption enhancer, and a cohesive strength improvement agent;
      wherein said cohesive strength improvement agent comprises a maleic anhydride group-containing polymer and a hydrophilic silicic anhydride, with the proportions of said hydrophilic silicic anhydride and said maleic anhydride group-containing copolymer accounting for 2 to 20 weight % and 0.1 to 10 weight %, respectively, of the adhesive layer.

2. A percutaneous pharmaceutical preparation prepared by laminating an adhesive layer comprising an adhesive and an active ingredient to one side of a backing material,
   wherein said adhesive is a copolymer composed of 20 to 55 mole % of vinylpyrrolidone and 80 to 45 mole % of a $C_4$ to $C_{18}$-alkyl ester of (meth)acrylic acid,
   said active ingredient is at least one member selected from the group consisting of norethisterone, estradiol, and their pharmacologically acceptable esters, and
   said adhesive layer further comprises:
      at least one member selected from the group consisting of dicarboxylic acids, hydroxy carboxylic acids, polyoxyethylene alkyl alcohol ethers, fatty acid ethanolamide compounds and N-acylsarcosines in a proportion of 0.1 to 10 weight %, based on the adhesive layer, as an absorption enhancer,
      a higher fatty acid ester prepared from a fatty acid having 10 to 18 carbon atoms and an alcohol having 1 to 20 carbon atoms in a proportion of 5 to 40 weight %, based on said adhesive layer, as another absorption enhancer, and a cohesive strength improvement agent;
      wherein said cohesive strength improvement agent comprises either a polyethylene powder with a particle diameter of not greater than 50 $\mu$m or a polyethylene fiber with a monofilament length of not greater than 1 mm and a maleic anhydride group-containing copolymer, the proportion of said polyethylene powder with a particle diameter of not greater than 50 $\mu$m or polyethylene fiber with a monofilament length of not greater than 1 mm accounting for 5 to 25 weight % of the adhesive layer and the proportion of said maleic anhydride group-containing copolymer accounting for 0.1 to 10 weight % of the adhesive layer.

3. A percutaneous pharmaceutical preparation prepared by laminating an adhesive layer comprising an adhesive and an active ingredient to one side of a backing material,
   wherein said adhesive is a copolymer composed of 20 to 55 mole % of vinylpyrrolidone and 80 to 45 mole % of a $C_4$ to $C_{18}$-alkyl ester of (meth)acrylic acid,
   said active ingredient is at least one member selected from the group consisting of norethisterone, estradiol, and their pharmacologically acceptable esters, and said adhesive layer further comprises:
  at least one member selected from the group consisting of dicarboxylic acids, hydroxy carboxylic acids, polyoxyethylene alkyl alcohol ethers, fatty acid ethanolamide compounds and N-acylsarcosines in a proportion of 0.1 to 10 weight %, based on the adhesive layer, as an absorption enhancer,
  a higher fatty acid ester prepared from a fatty acid having 10 to 18 carbon atoms and an alcohol having 1 to 20 carbon atoms in a proportion of 5 to 40 weight %, based on said adhesive layer, as another absorption enhancer, and a cohesive strength improvement agent;
  wherein the cohesive strength improvement agent comprises a hydrophilic silicic anhydride and a polyhydric alcohol, with the proportions of said hydrophilic silicic anhydride and said polyhydric alcohol accounting for 2 to 20 weight % and 1 to 40 weight %, respectively, of the adhesive layer.

4. A percutaneous pharmaceutical preparation prepared by laminating an adhesive layer comprising an adhesive and an active ingredient to one side of a backing material,
  wherein said adhesive is a copolymer composed of 20 to 55 mole % of vinylpyrrolidone and 80 to 45 mole % of a $C_4$ to $C_{18}$-alkyl ester of (meth)acrylic acid,
  said active ingredient is at least one member selected from the group consisting of norethisterone, estradiol, and their pharmacologically acceptable esters, and
  said adhesive layer further comprises:
    at least one member selected from the group consisting of dicarboxylic acids, hydroxy carboxylic acids, polyoxyethylene alkyl alcohol ethers, fatty acid ethanolamide compounds and N-acylsarcosines in a proportion of 0.1 to 10 weight %, based on the adhesive layer, as an absorption enhancer,
    a higher fatty acid ester prepared from a fatty acid having 10 to 18 carbon atoms and an alcohol having 1 to 20 carbon atoms in a proportion of 5 to 40 weight %, based on said adhesive layer, as another absorption enhancer, and a cohesive strength improvement agent;
    wherein the cohesive strength improvement agent comprises a hydrophilic silicic anhydride and a polycarboxylic acid, with the proportions of said hydrophilic silicic anhydride and said polycarboxylic acid accounting for 2 to 20 weight % and 0.5 to 20 weight %, respectively, of the adhesive layer.

* * * * *